(12) United States Patent  
Danner et al.

(10) Patent No.: US 9,328,054 B1  
(45) Date of Patent: May 3, 2016

(54) METHOD OF ALCOHOLISIS OF FATTY ACIDS AND FATTY ACID GYICERIDES

(71) Applicants: Travis Danner, South Pittsburg, TN (US); Philip N. Brown, Boulder, CO (US); Mark Mauss, Lookout Mountain, TN (US)

(72) Inventors: Travis Danner, South Pittsburg, TN (US); Philip N. Brown, Boulder, CO (US); Mark Mauss, Lookout Mountain, TN (US)

(*) Notice: Subject to any disclaimer, the term of this patent is extended or adjusted under 35 U.S.C. 154(b) by 0 days.

(21) Appl. No.: 14/498,387

(22) Filed: Sep. 26, 2014

Related U.S. Application Data

(60) Provisional application No. 61/883,722, filed on Sep. 27, 2013.

(51) Int. Cl.
| | | |
|---|---|---|
| *C07C 67/02* | (2006.01) | |
| *C07C 67/03* | (2006.01) | |
| *C07C 69/00* | (2006.01) | |
| *C07C 67/08* | (2006.01) | |

(52) U.S. Cl.
CPC .............. *C07C 67/08* (2013.01); *C07C 67/02* (2013.01)

(58) Field of Classification Search
CPC .......... C07C 67/02; C07C 67/08; C07C 67/03
See application file for complete search history.

(56) References Cited

U.S. PATENT DOCUMENTS

| | | |
|---|---|---|
| 1,228,888 A | 6/1917 | Dreymann |
| 1,421,605 A | 7/1922 | Steffens |
| 1,651,666 A | 12/1927 | Buc |
| 1,701,703 A | 2/1929 | Starrels |
| 2,177,407 A | 10/1939 | Hansley |
| 2,271,619 A | 2/1942 | Bradshaw et al. |
| 2,290,609 A | 7/1942 | Goss et al. |
| 2,383,579 A | 8/1945 | Allen et al. |
| 2,383,599 A | 8/1945 | Glossop |
| 2,383,601 A | 8/1945 | Kelm |
| RE22,751 E | 4/1946 | Trent |
| 2,447,186 A | 8/1948 | King et al. |
| 2,486,444 A | 11/1949 | Smith |
| 2,486,938 A | 11/1949 | Fish |
| 2,494,366 A | 1/1950 | Sprules et al. |
| 2,521,742 A | 9/1950 | Paterson |
| 2,543,421 A | 2/1951 | Price et al. |
| 2,727,049 A | 12/1955 | Braconier et al. |
| 3,383,396 A | 5/1968 | Cahn et al. |
| 3,474,131 A | 10/1969 | Schmerling |
| 3,496,159 A | 2/1970 | Spence |
| 3,816,485 A | 6/1974 | Wechsler |
| 3,927,982 A | 12/1975 | Chapman et al. |
| 4,032,550 A | 6/1977 | White et al. |
| 4,112,235 A | 9/1978 | Schmerling |
| 4,164,506 A | 8/1979 | Kawahara et al. |
| 4,216,337 A | 8/1980 | Baba et al. |
| 4,229,362 A | 10/1980 | Norman |
| 4,266,076 A | 5/1981 | Gruffaz et al. |
| 4,281,176 A | 7/1981 | Gruffaz et al. |
| 4,297,291 A | 10/1981 | Lionelle et al. |
| 4,303,590 A | 12/1981 | Tanaka et al. |
| 4,371,470 A | 2/1983 | Matsukura et al. |
| 4,381,407 A | 4/1983 | Bremus et al. |
| 4,397,655 A | 8/1983 | Sweeney |
| 4,487,933 A | 12/1984 | Mixan |
| 4,552,702 A | 11/1985 | Schmid et al. |
| 4,608,202 A | 8/1986 | Lepper et al. |
| 4,650,611 A | 3/1987 | Schmid |
| 4,652,406 A | 3/1987 | Lepper et al. |
| 4,668,439 A | 5/1987 | Billenstein et al. |
| 4,695,411 A | 9/1987 | Stern et al. |
| 4,698,186 A | 10/1987 | Jeromin et al. |
| 4,839,287 A | 6/1989 | Holmberg et al. |
| 4,889,950 A | 12/1989 | Bott et al. |
| 4,956,286 A | 9/1990 | Macrae |
| 4,976,892 A | 12/1990 | Jeromin et al. |
| 5,008,046 A | 4/1991 | Bremus et al. |
| 5,116,546 A | 5/1992 | Klok et al. |
| 5,130,061 A | 7/1992 | Cornieri et al. |
| 5,219,733 A | 6/1993 | Myojo et al. |
| 5,288,619 A | 2/1994 | Brown et al. |
| 5,349,075 A | 9/1994 | van den Berg et al. |
| 5,350,879 A | 9/1994 | Engel et al. |
| 5,354,878 A | 10/1994 | Connemann et al. |
| 5,389,113 A | 2/1995 | Demmering et al. |
| 5,399,731 A | 3/1995 | Wimmer |
| 5,405,992 A | 4/1995 | Funk et al. |
| 5,424,466 A | 6/1995 | Stern et al. |
| 5,426,199 A | 6/1995 | Lundquist |
| 5,434,279 A | 7/1995 | Wimmer |
| 5,455,370 A | 10/1995 | Demmering et al. |
| 5,468,887 A | 11/1995 | Gupta |
| 5,480,707 A | 1/1996 | Steffier |
| 5,508,457 A | 4/1996 | Bayense et al. |
| 5,514,820 A | 5/1996 | Assmann et al. |
| 5,525,126 A | 6/1996 | Basu et al. |
| 5,532,392 A | 7/1996 | Gheorghiu |
| 5,578,090 A | 11/1996 | Bradin |
| 5,710,030 A | 1/1998 | Anderson |
| 5,713,965 A | 2/1998 | Foglia et al. |
| 5,730,029 A | 3/1998 | Stoldt et al. |
| 5,773,636 A | 6/1998 | Demmering et al. |
| 5,844,111 A | 12/1998 | Granberg et al. |
| 5,849,939 A | 12/1998 | Mittelbach et al. |
| 5,885,946 A | 3/1999 | Lamsa |
| 5,908,946 A | 6/1999 | Stern et al. |
| 5,972,057 A | 10/1999 | Hayafuji et al. |

(Continued)

*Primary Examiner* — Yong Chu
(74) *Attorney, Agent, or Firm* — Stephen J. Stark; Miller & Martin PLLC

(57) ABSTRACT

At least one of transesterification, esterification and hydrolysis can occur with a method as shown and described herein. Preferably pressures are lower than supercritical pressures for the alcohol employed and the conversion rate is at least 95%, if not 99% in a single reactor which may be counter or co-flow or even a batch process. Meanwhile, bound glycerin may be separated from alkyl esters for at least some processes.

15 Claims, 2 Drawing Sheets

(56) References Cited

U.S. PATENT DOCUMENTS

| | | |
|---|---|---|
| 6,013,114 A | 1/2000 | Hille et al. |
| 6,013,817 A | 1/2000 | Stern et al. |
| 6,015,440 A | 1/2000 | Noureddini |
| 6,028,215 A | 2/2000 | Bessling et al. |
| 6,069,261 A | 5/2000 | Hoffmann et al. |
| 6,090,959 A | 7/2000 | Hirano et al. |
| 6,127,560 A | 10/2000 | Stidham et al. |
| 6,147,196 A | 11/2000 | Stern et al. |
| 6,174,501 B1 | 1/2001 | Noureddini |
| 6,187,939 B1 | 2/2001 | Sasaki et al. |
| 6,211,390 B1 | 4/2001 | Peter et al. |
| 6,262,285 B1 | 7/2001 | McDonald |
| 6,288,251 B1 | 9/2001 | Tsuto et al. |
| 6,359,157 B2 | 3/2002 | Peter et al. |
| 6,398,707 B1 | 6/2002 | Wu et al. |
| 6,399,800 B1 | 6/2002 | Haas et al. |
| 6,407,269 B2 | 6/2002 | Kaita et al. |
| 6,440,057 B1 | 8/2002 | Ergun et al. |
| 6,489,496 B2 | 12/2002 | Barnhorst et al. |
| 6,509,487 B2 | 1/2003 | Tatsumi et al. |
| 6,538,146 B2 | 3/2003 | Turck |
| 6,570,030 B2 | 5/2003 | Goto et al. |
| 6,635,595 B2 | 10/2003 | Kaimal et al. |
| 6,642,399 B2 | 11/2003 | Boocock |
| 6,696,583 B2 | 2/2004 | Koncar et al. |
| 6,712,867 B1 | 3/2004 | Boocock |
| 6,768,015 B1 | 7/2004 | Luxem et al. |
| 6,812,359 B2 | 11/2004 | Goto et al. |
| 6,818,026 B2 | 11/2004 | Tateno et al. |
| 6,822,105 B1 | 11/2004 | Luxem et al. |
| 6,855,838 B2 | 2/2005 | Haas et al. |
| 6,878,837 B2 | 4/2005 | Bournay et al. |
| 6,884,900 B2 | 4/2005 | Maeda et al. |
| 6,887,283 B1 | 5/2005 | Ginosar et al. |
| 6,897,328 B2 | 5/2005 | Gutsche et al. |
| 6,933,398 B2 | 8/2005 | Peter et al. |
| 6,960,672 B2 | 11/2005 | Nakayama et al. |
| 6,960,673 B2 | 11/2005 | Brunner et al. |
| 6,965,043 B1 | 11/2005 | Kenneally et al. |
| 6,965,044 B1 | 11/2005 | Hammond et al. |
| 6,979,426 B2 | 12/2005 | Teall et al. |
| 6,982,155 B1 | 1/2006 | Fukuda et al. |
| 6,982,340 B2 | 1/2006 | Mumura et al. |
| 7,045,100 B2 | 5/2006 | Ergun et al. |
| 7,087,771 B2 | 8/2006 | Luxem et al. |
| 7,091,367 B2 | 8/2006 | Moritz et al. |
| 7,109,363 B2 | 9/2006 | Brunner et al. |
| 7,112,229 B2 | 9/2006 | Khalil et al. |
| 7,122,688 B2 | 10/2006 | Lin et al. |
| 7,138,536 B2 | 11/2006 | Bournay et al. |
| 7,145,026 B2 | 12/2006 | Fleisher |
| 7,151,187 B2 | 12/2006 | Delfort et al. |
| 7,211,681 B2 | 5/2007 | Furuta |
| 7,227,030 B2 | 6/2007 | Saka |
| 7,247,739 B2 | 7/2007 | Gapes et al. |
| 7,252,779 B2 | 8/2007 | Mosier et al. |
| 7,256,301 B2 | 8/2007 | Erguen et al. |
| 7,271,275 B2 | 9/2007 | Katayama et al. |
| 7,312,355 B2 | 12/2007 | Corma Canos et al. |
| 7,321,052 B2 | 1/2008 | Miller et al. |
| 7,420,072 B2 | 9/2008 | Fleisher |
| 7,420,073 B2 | 9/2008 | Hillion et al. |
| 7,452,515 B1 | 11/2008 | Lafleur et al. |
| 7,456,305 B2 | 11/2008 | Piacentini et al. |
| 7,468,450 B2 | 12/2008 | Peter et al. |
| 7,473,539 B2 | 1/2009 | Chou |
| 7,481,981 B2 | 1/2009 | Moritz et al. |
| 7,488,837 B2 | 2/2009 | Tsuto et al. |
| 7,498,454 B2 | 3/2009 | Redlingshoefer et al. |
| 7,507,846 B2 | 3/2009 | Pelly |
| 7,514,575 B2 | 4/2009 | Ginosar et al. |
| 7,524,982 B2 | 4/2009 | DallAgnol et al. |
| 7,528,272 B2 | 5/2009 | Alasti |
| 7,544,830 B2 | 6/2009 | Parnas et al. |
| 7,547,539 B2 | 6/2009 | Ikegami et al. |
| 7,550,614 B2 | 6/2009 | Banavali et al. |
| 7,563,915 B2 | 7/2009 | Matson et al. |
| 7,566,794 B2 | 7/2009 | Hillion et al. |
| 7,582,784 B2 | 9/2009 | Banavali et al. |
| 7,605,281 B2 | 10/2009 | Oku et al. |
| 7,612,221 B2 | 11/2009 | Haas et al. |
| 7,619,104 B2 | 11/2009 | Clements |
| 7,622,600 B1 | 11/2009 | Marr |
| 7,626,047 B2 | 12/2009 | Nakayama et al. |
| 7,637,969 B2 | 12/2009 | Delgado Puche |
| 7,638,314 B2 | 12/2009 | Zappi et al. |
| 7,652,156 B2 | 1/2010 | Hillion et al. |
| 7,655,055 B2 | 2/2010 | Waynick |
| 7,667,068 B2 | 2/2010 | Miller et al. |
| 7,691,159 B2 | 4/2010 | Li |
| 7,691,270 B2 | 4/2010 | Ginosar et al. |
| 7,695,533 B2 | 4/2010 | Kovacs et al. |
| 7,696,376 B2 | 4/2010 | Furuta |
| 7,700,793 B2 | 4/2010 | Iyer |
| 7,705,170 B2 | 4/2010 | Geier et al. |
| 7,722,755 B2 | 5/2010 | Lawson et al. |
| 7,754,643 B2 | 7/2010 | Sriniuas et al. |
| 7,754,905 B2 | 7/2010 | Kozyuk |
| 7,767,837 B2 | 8/2010 | Elliott |
| 7,772,414 B1 | 8/2010 | Hybertson et al. |
| 7,790,651 B2 | 9/2010 | Lin et al. |
| 7,795,460 B2 | 9/2010 | Elliott |
| 7,806,945 B2 | 10/2010 | Jackam et al. |
| 7,812,187 B2 | 10/2010 | Kawashima et al. |
| 7,828,978 B2 | 11/2010 | Geier et al. |
| 7,834,203 B2 | 11/2010 | Lee et al. |
| 7,851,643 B2 | 12/2010 | Hillion et al. |
| 7,857,869 B2 | 12/2010 | Tsuto et al. |
| 7,871,448 B2 | 1/2011 | Jackam et al. |
| 7,872,149 B2 | 1/2011 | Bunning et al. |
| 7,888,520 B2 | 2/2011 | Reaney et al. |
| 7,897,798 B2 | 3/2011 | McNeff et al. |
| 7,905,931 B2 | 3/2011 | Woods et al. |
| 7,906,082 B2 | 3/2011 | Pelly |
| 7,906,665 B2 | 3/2011 | Lin et al. |
| 7,935,157 B2 | 5/2011 | Kozyuk et al. |
| 7,943,792 B2 | 5/2011 | Berry et al. |
| 7,951,967 B2 | 5/2011 | Chun et al. |
| 2006/0052619 A1* | 3/2006 | Gutsche ............... C07C 67/08 554/174 |
| 2010/0130769 A1* | 5/2010 | Banavali et al. ............ 560/129 |

* cited by examiner

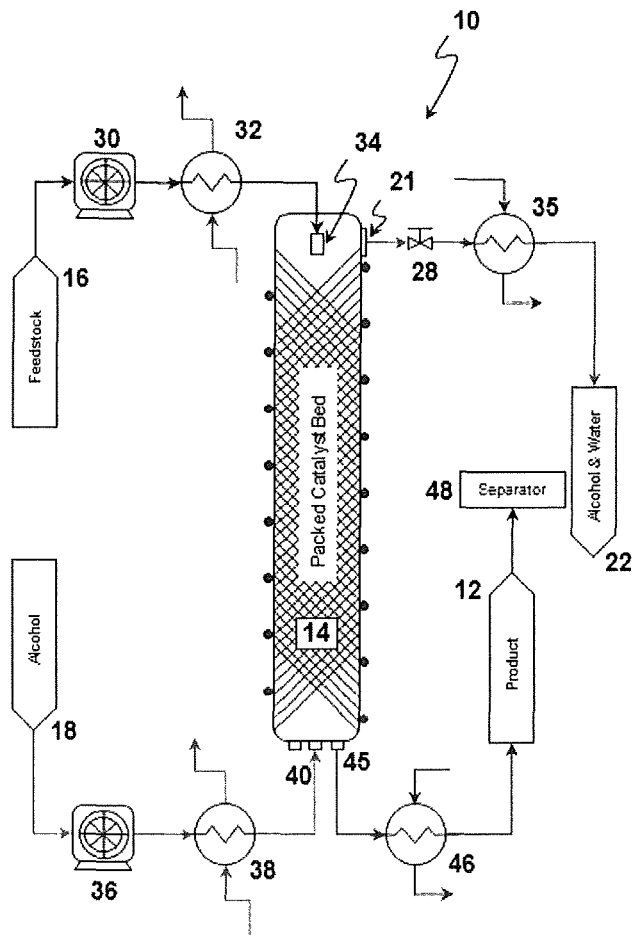
Figure 1: Counterflow reactor schematic

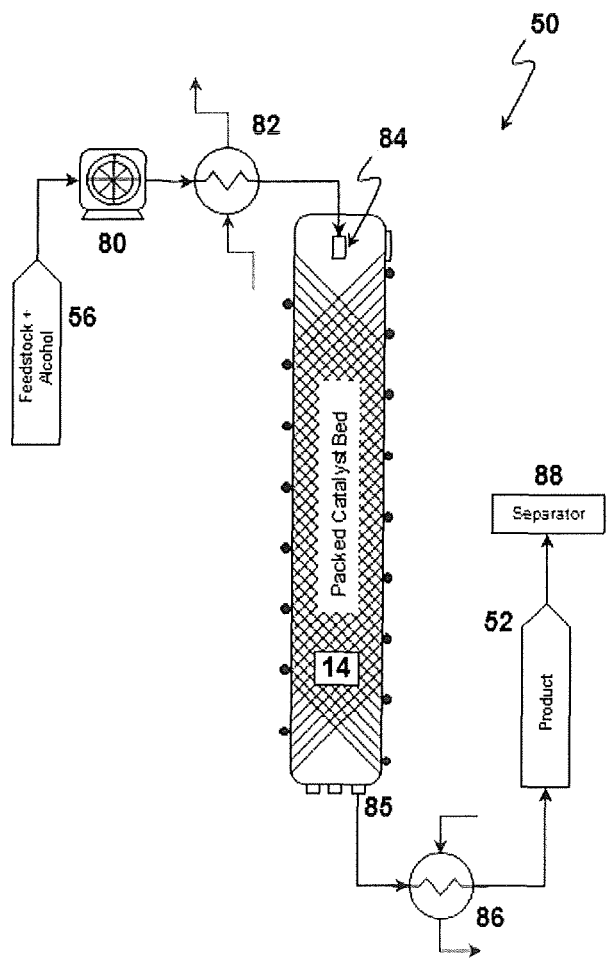
Figure 2: Co-flow Reactor Schematic
Figure 3: Embodiement color improvement

METHOD OF ALCOHOLISIS OF FATTY ACIDS AND FATTY ACID GYICERIDES

CLAIM OF PRIORITY

This application claims the benefit of U.S. Provisional Patent Application No. 61/883,722 filed Sep. 27, 2013 which is incorporated herein by reference in its entirety.

FIELD OF THE INVENTION

This application relates to such methods performed preferably by using a counter flow, vapor-phase alcohol, heterogeneous catalyst process and more particularly for at least some embodiments to a less than supercritical pressure for the alcohol, fatty acid ester production process.

BACKGROUND OF THE INVENTION

Many parties have attempted various technologies to esterify free fatty acids and to transesterify fatty acid glycerides, such as from waste vegetable oil and other products to provide alkyl esters for further industrial use, even for use as renewable fuels. However, all prior art processes are believed to be able to be improved.

SUMMARY OF THE INVENTION

It is an object of many embodiments of the present invention to provide improved processes.

One embodiment of a chemical process proposed herein preferably uses superheated alcohols at preferably moderately low pressures, such as less than supercritical pressures, such as about 1150 psig for methanol (but of course, other alcohols could be utilized with various embodiments), for the esterification of free fatty acids and/or the transesterification of fatty acid glycerides in the production of fatty acid esters. These proposed processes may employ a heterogeneous catalyst that may maximize ester yield while also stripping impurities resulting in esters that may be lighter in color with fewer contaminants than other similar processes.

Unlike other near supercritical alcohol treatment systems that operate at elevated pressures—in excess of 500 prig, at least one embodiment of the system proposed herein can operate at pressures as low as ambient, although higher pressure embodiments may be utilized as well. As a result the capital cost of the equipment required for some preferred embodiments of the proposed process may be much lower than that for supercritical treatment systems requiring high pressure equipment for those embodiments. Additionally, most supercritical processes are known to require 800% excess alcohol or more as compared to most conventional systems that may require only up to about 100% excess alcohol. Higher alcohol concentrations may require additional energy and equipment to recover that excess alcohol.

The superheated alcohol treatment process of many preferred embodiments proposed herein can operate over a wide range of excess alcohol fractions and for at least some embodiments can be done in such a manner as to possibly nearly eliminate the need for additional energy and equipment to recover the excess alcohol (or other alcohol) because the alcohol may be superheated so it can remain in the reactor while the product alkyl esters and by-product glycerin can exit the reactor with minimal alcohol in the product mixture. The process may require both lower variable and capital costs as compared to most conventional and near critical production processes and simultaneously allow for the treatment of lower grade, highly contaminated raw materials.

BRIEF DESCRIPTION OF THE DRAWINGS

The particular features and advantages of the invention as well as other objects will become apparent from the following description taken in connection with the accompanying drawings in which:

FIG. 1 is a schematic view of a continuous counter-flow superheated reactor according to a presently preferred embodiment; and FIG. 2 is a schematic view of a continuous co-flow superheated reactor according to a alternatively presently preferred embodiment; and FIG. 3 is a drawing showing a change in color of feedstock according to at least some embodiments of the present invention.

DETAILED DESCRIPTION OF THE PREFERRED EMBODIMENTS

The applicant conducted exploratory testing of supercritical and superheated methanol transesterification and esterification processes both in batch and continuous reactors. Table 1 and Table 2 summarize the batched testing conducted in a Parr (batch) reactor. Table 1 displays conditions and results for single stage reactions and for the first stage of several two stage reactions; Table 2 displays data for the second stage of those two stage reactions conducted—B. Gly is the product bound glycerin.

TABLE 1

Single stage (or first stage) reactions

| Date | Feedstock | Sample Size [g] | Methanol [% wt of oil] | Time >450 F. [min] | Max Temp [F.] | Max Press [psig] | B. Gly [% wt] | Sulfuric [% wt of oi] |
|---|---|---|---|---|---|---|---|---|
| Aug. 20, 2009 | Canola | 158 | 227% | — | 642 | 2600 | 0.43% | 0 |
| Aug. 21, 2009 | Canola | 169 | 138% | 90 | 707 | 2075 | 0.35% | 0 |
| Aug. 21, 2009 | Canola | 75 | 311% | 77 | 707 | 2180 | 0.067% | 0 |
| Aug. 22, 2009 | Turkey | 170 | 138% | — | 662 | — | 0.710% | 0 |
| Aug. 24, 2009 | Canola | 224 | 82% | — | 662 | — | 0.160% | 1% |
| Aug. 24, 2009 | Canola* | 224 | 34% | >30 | 680 | 690 | 1.510% | 0 |
| Aug. 25, 2009 | Canola* | 225 | 51% | >22 | 654 | 920 | 1.510% | 0 |
| Aug. 27, 2009*** | Canola* | 235 | 34% | 100 | 660 | 655 | 0.87%** | 0 |
| Aug. 28, 2009*** | Canola* | 267 | 20% | — | 687 | 400 | 1.660% | 0 |
| — | Canola* | — | 20% | — | 572 | — | 3.550% | 0 |

*Entries have a corresponding second stage in Table 2 below
**SafeTest results may have been reading 60%-85% of actual
***A vacuum was pulled on the reactor before starting

TABLE 2

Second stage reactions

| Date | Feedstock | Sample Size [g] | Methanol [% wt of oil] | Time >450 F. [min] | Max Temp [F.] | Max Press [psig] | B. Gly [% wt] | Catalyst [% wt of oil] |
|---|---|---|---|---|---|---|---|---|
| Aug. 24, 2009 | Canola | 194 | 55% | — | 631 | 1020 | 0.210% | 0 |
| Aug. 25, 2009 | Canola | 200 | 50% | — | — | — | 0.320% | 0 |
| Aug. 27, 2009 | Canola | 224 | 34% | >10 | >608 | 770 | 0.20%** | 0 |
| Aug. 28, 2009* | Canala | 260 | 20% | — | 678 | 460 | 0.190% | 0 |
| — | Canola | — | 20% | — | 572 | — | 1.570% | 0 |

*A third stage with 20% methanol was conducted on the products of this reaction resulting in 0.00% BG From this data, it was hypothesized that a continuous reactor 10 wherein feedstock 16 is slowly dripped through superheated methanol, or other monohydric aliphatic alcohol, at low pressure (less than 1000 psig, if not less than 200 psig, 150 psig, 100 psig, or even ambient) could prove to be a very effective and low cost approach to both transesterification and esterification. A small (2" diameter×40" long) lab scale continuous reactor 10 was constructed, randomly packed with stainless steel windings as catalyst 14. Preliminary testing was conducted in this reactor 10; the results from testing are shown in Table 3—AN is the product acid number,

TABLE 3

Test results from the first generation continuous superheated reactor

| Feedstock | Approx Rate [g/min] | Temp [F.] | Max Press [psig] | AN | B. Gly [% wt] |
|---|---|---|---|---|---|
| 15.7% FFA Soapstock | 1.6 | 500 | 145 | 0.76 | <0.2 |
| Refined Turkey | 1-2 | 500 | 150 | | 0.500% |
| Refined Turkey | 1-2 | 425 | 180-190 | | 5.531% |

TABLE 3-continued

Test results from the first generation continuous superheated reactor

| Feedstock | Approx Rate [g/min] | Temp [F.] | Max Press [psig] | AN | B. Gly [% wt] |
|---|---|---|---|---|---|
| Refined Turkey | 1-2 | 450 | 180-190 | | 0.856% |
| Refined Turkey | 1-2 | 475 | 180-190 | | 0.926% |

These initial results show great potential for this approach and support the need for further investigation. Factors that may have influenced completion that could not be controlled or quantified in this first generation reactor 10 were: partial oxidation of feedstock 16 due to entrained air, precise temperature control throughout the entire reactor 10, catalytic value of packing. These initial results showed great promise and warranted additional investigation.

A second generation continuous reactor 10 was constructed that provided the flexibility to: more precisely control reactor 10 and reactant temperatures throughout the entire process, test various reactor sizes and aspect ratios, test various catalyst compositions and form factors to provide as catalyst 14, more precisely control reactant flow rates over a wider flow regime minimizing air/oxygen entrainment.

FIG. 1 provides a schematic of the development apparatus. Test results from this second generation development reactor are shown in Table 4.

TABLE 4

Test results from the second generation continuous superheated reactor

| Feedstock | Reactor [dia × len] | Catalyst | Feedstock [g/min] | Methanol [%] | Temp [F.] | Pressure [psig] | AN |
|---|---|---|---|---|---|---|---|
| Acid Oil, AN 72 | 2" × 18" | Alumina Substrate, 1/8" spheres | 20 | 40% | 300 | 95 | 60.0 |
| Acid Oil, AN 72 | 2" × 18" | 0.1% Pt on Alumina Substrate, 1/8" spheres | 40 | 20% | 500 | 125 | 41.4 |
| Acid Oil, AN 72 | 2" × 18" | 0.1% Pd on Alumina Substrate, 1/8" spheres | 20 | 25% | 300 | 75 | 36.0 |
| Acid Oil, AN 72 | 2" × 18" | 0.1% Pd on Alumina Substrate, 1/8" spheres | 40 | 20% | 400 | 100 | 35.0 |
| Acid Oil, AN 72 | 1" × 46" | Silica Zeolite, 0.17 Spheres | 25 | 32% | 400 | 120 | 34.4 |
| Acid Oil, AN 72 | 2" × 18" | Alumina Substrate, 1/8" spheres | 40 | 20% | 400 | 130 | 34.0 |
| Acid Oil, AN 72 | 2" × 18" | Alumina Substrate, 1/8" spheres | 40 | 20% | 500 | 130 | 31.6 |
| Acid Oil, AN 72 | 2" × 18" | 0.1% Pt on Alumina Substrate, 1/8" spheres | 40 | 20% | 575 | 125 | 30.2 |
| Acid Oil, AN 72 | 2" × 18" | 0.1% Pd on Alumina Substrate, 1/8" spheres | 40 | 13% | 500 | 125 | 28.0 |
| Acid Oil, AN 72 | 1" × 46" | NiO on Alumina Substrate, 1/8" cylinders | 15 | 53% | 400 | 130 | 21.6 |
| Acid Oil, AN 72 | 1" × 46" | Silica Zeolite, 0.17 Spheres | 29 | 28% | 500 | 120 | 13.2 |
| Acid Oil, AN 72 | 2" × 18" | Alumina Substrate,1/8" spheres | 40 | 20% | 575 | 130 | 14.2 |
| Acid Oil, AN 72 | 2" × 18" | NiO on Alumina Substrate, 1/8" cylinders | 56 | 14% | 575 | 130 | 12.4 |
| Acid Oil, AN 72 | 2" × 18" | 0.1% Pd on Alumina Substrate, 1/8" spheres | 40 | 20% | 575 | 125 | 12.2 |
| Acid Oil, AN 72 | 1" × 46" | Activated Clay | 11 | 73% | 300 | 150 | 7.6 |
| Acid Oil, AN 72 | 2" × 18" | 1.5 lb, 34 AWG Ni200 Wire | 45 | 18% | 535 | 130 | 7.2 |
| Acid Oil, AN 72 | 1" × 46" | Activated Clay | 8 | 88% | 400 | 140 | 7.0 |
| Acid Oil, AN 72 | 1" × 46" | Silica Zeolite, 0.17 Spheres | 24 | 33% | 575 | 120 | 6.4 |
| Acid Oil, AN 72 | 2" × 18" | 0.1% Pd on Alumina Substrate, 1/8" spheres | 40 | 20% | 600 | 130 | 6.3 |
| Trap Grease, AN 198 | 1" × 46" | Activated Clay | 11 | 45% | 300 | 100 | 16.6 |
| Acid Oil, AN 72 | 2" × 18" | 1.5 lb, 34 AWG Ni200 Wire | 30 | 27% | 575 | 130 | 5.2 |
| Acid Oil, AN 72 | 1" × 46" | NiO on Alumina Substrate, 1/8" cylinders | 15 | 53% | 500 | 130 | 3.8 |
| Trap Grease, AN 160 | 2" × 40" | Stainless Steel 316 Wool, 0.002" dia | 40 | 25% | 550 | 185 | 7.2 |
| Acid Oil, AN 144 | 2" × 40" | Stainless Steel 316 Wool, 0.002" dia | 40 | 25% | 550 | 160 | 6.4 |
| Trap Grease, AN 198 | 1" × 46" | Activated Clay | 12 | 42% | 400 | 130 | 7.4 |

TABLE 4-continued

Test results from the second generation continuous superheated reactor

| Feedstock | Reactor [dia × len] | Catalyst | Feedstock [g/min] | Methanol [%] | Temp [F.] | Pressure [psig] | AN |
|---|---|---|---|---|---|---|---|
| Acid Oil, AN 72 | 2" × 18" | NiO on Alumina Substrate, 1/8" cylinders | 25 | 32% | 575 | 130 | 1.5 |
| Acid Oil, AN 144 | 2" × 40" | Stainless Steel 316 Wool, 0.002" dia | 40 | 25% | 575 | 160 | 2.4 |
| Acid Oil, AN 72 | 1" × 46" | Silica Zeolite, 0.17 Spheres | 14 | 36% | 575 | 120 | 1.1 |
| Acid Oil, AN 72 | 1" × 46" | NiO on Alumina Substrate, 1/8" cylinders | 15 | 53% | 575 | 130 | 0.5 |
| Acid Oil, AN 72 | 1" × 46" | Activated Clay | 9 | 78% | 575 | 140 | 0.5 |
| Acid Oil, AN 72 | 1" × 46" | Activated Clay | 9 | 78% | 500 | 140 | 0.3 |
| Trap Grease, AN 198 | 1" × 46" | Activated Clay | 12 | 42% | 450 | 130 | 0.22 |

The results in Table 4 have been ordered from top to bottom according to the lowest rate of conversion to the highest rate of conversion—tests near the bottom of the table may hold the greatest potential for commercialization for at least some embodiments. Of all catalysts 14 an activated clay product as described herein provided the absolute lowest acid number (0.22) of the exiting product 12. The activated clay was prepared in granular form and activated with citric acid; phosphorous acid or sulfuric acid, although other acids could likely be used as well. The chemical composition of the catalyst 14 may be provided as about 50-90% $SiO_2$, about 0-9% $Fe_2O_3$, about 1-15% $Al_2O_3$, about 0-5% CaO, about 0-5% MgO, about 0-5% $Na_2O$, about 0-5% of $K_2O$, about 0-5% $TiO_2$, up to 10% other, and about 0-15% Ignition Loss. In addition to achieving the lowest acid number of any other catalyst, the catalyst also: met the ASTM D6751 acid number specification for renewable diesel (<0.5) at a reaction temperature that was over a hundred degrees cooler than any other catalyst tested, resulted in a product 12 that was several shades lighter in color than the ingoing feedstock 16 (see FIG. 3), and reduced sulfur content from over 40 ppm in the ingoing feedstock to under 5 ppm in the final product.

Another way to describe this activated clay would be having a surface area of 180 to 300 m2/g; a total pore volume of 0.5 to 0.7 ml/g; wherein at least 60% of the total pore volume are provided by pores having a pore diameter of at least 140 Å, at least 40% of the total pore volume is provided by pores having a pore diameter of less than 250 Å and at least 15% of the total pore volume are provided by pores having a pore diameter of 140 to 250 Å and less than 20% of the total pore volume is formed by pores having a diameter of >800 Å; a $SiO_2$ content of between more than 60 wt. % and less than 75 wt. %; an aluminum content, calculated as $Al_2O_3$, of between less than 12 wt. % and more than 2 wt. %; and said clay material having an amorphous structure according to XRD data. Other embodiments may employ catalysts having different degrees of porosity.

This activated clay may be acid activated with an acid selected from the group of phosphoric acid, sulphuric acid and citric acid, and the acid activation step occurs by depositing an acid on the clay and the amount of acid deposited on the clay material is selected within a range of 2 to 5 wt.-%, calculated as water-free acid and based on the weight of the dry clay material. The clay may also be base activated for at least some embodiments. Preferred clay preparation includes activation with sodium, potassium, magnesium, and/or calcium hydroxides.

The process development and testing that has been conducted to date demonstrates that a counter current reactor column reactor 10 packed with an appropriate catalyst 14 wherein fats, oils and/or greases from feedstock 16 trickle down through the catalyst 14 while superheated alcohol such as methanol 18 flows upward sweeping byproduct water with it out port 21 as vapor 22 which in this embodiment would be methanol and water with it is a very effective approach for both the transesterification of fatty acid glycerides as well as the esterification of fatty acids; in both cases to provide product 12, degrees of completion can be achieved that exceed the ASTM D6751 standard for renewable diesel or other alkyl ester product. Moreover, through careful selection of catalyst 14, improvements in color and reduction of detrimental contaminates can be realized in so eliminating costly additional processing steps to achieve similar levels of ester quality and purity.

Feedstock 16 from a supply can be pumped with pump 30, and/or possibly directed through heat exchanger 32 to then enter reactor at inlet 34. Alcohol 18 can be directed through pump 36, and/or possibly through heat exchanger 38 to inlet 40. The vapor 22 leaving from port 21 may be directed through valve 42 and/or heat exchanger 44 (which may cool and even use the heat to at least assist in heating feedstock and/or input alcohol). Product 12 may be cooled after with heat exchanger 46 exiting outlet 45 and may possibly be pumped and/or directed to separator 48 to assist in separating released glycerin from alkyl esters, for at least some embodiments.

The proposed process has significant benefit for the production of alkyl esters from a broad range of feedstocks 16. Production costs of alkyl esters from high grade feedstocks 16 such as crude vegetable oils or even refined, bleached, and degummed vegetable oils which are easily processed in conventional base-transesterification can be significantly reduced by employing the proposed process thereby significantly reducing one of the largest variable costs—the base catalyst 14. For most production facilities this may result in savings on the order of $0.03-$0.05 per gallon of alkyl esters produced. Additionally the byproduct glycerin from this process would be in excess of 95% purity versus typical purity of less than 80% from a conventional process; this increase in glycerin purity adds approximately $0.03-$0.05 additional revenue per gallon of alkyl esters produced. The total additional value for even the cleanest feedstocks 16 employing the proposed process over conventional process is estimated to be between $0.06 and $0.1 per gallon of alkyl esters produced. Products 12 from a transesterification process are expected to be both alkyl esters as well as free glycerin which can be removed mechanically (such as through various separation techniques as are known in the art).

One of the greatest potentials for at least some embodiments of the proposed process, however, is in the production of alkyl esters from feedstocks 16 such as low grade fats and greases such as trap grease that cannot otherwise be processed in conventional or even other advanced process technologies, at least not without extensive preprocessing and post processing. These low grade feedstocks 16 may be characterized as those having high levels of: free fatty acids, sulfur, ash, metals, detergents, peroxides, etc. The process proposed herein performs many of the functions in one or two process stages that would typically require numerous process steps significantly reducing capital expenditure and variable cost in so enabling the production of alkyl esters from low grade feedstocks that were previously economically unviable to process.

One element of the physical implementation of many embodiments of this process is a counter current (or counter flow) packed column or reactor 10 wherein feedstock gravity drains from top to bottom (a first direction) while vapor alcohol and any byproduct water flow from bottom to top (a second direction). This approach provides for extremely high alcohol to oil molar ratios yet minimizes the alcohol in the exiting product stream. Other embodiments may have the process is implemented as transesterification—only, a single packed, co-flow column may be employed wherein the packing could be with a heterogeneous catalyst meeting the description of that outlined below.

FIG. 2 provides a schematic of such a co-flow reactor wherein feedstock and alcohol 56 from a supply can be pumped with pump 80, and/or possibly directed through heat exchanger 82 to then enter reactor at inlet 84. Product 52 may be cooled after with heat exchanger 86 exiting outlet 85 and may possibly be pumped and/or directed to separator 88 to assist in separating released glycerin from alkyl esters, for at least some embodiments. Table 5 provides experimental data resulting from operating such a reactor at various conditions with certain catalysts,

TABLE 5

Test results from a co-flow continuous superheated reactor

| Feedstock | Reactor [dia × len] | Catalyst | Feedstock [g/min] | Methanol [%] | Temp [F.] | Pressure [psig] | BG [%] | AN |
|---|---|---|---|---|---|---|---|---|
| Crude Soy, AN 1.4 | 0.5" × 12" | Base Acitivated Clay 226 | 0.5 | 35% | 475 | 500 | 0.88% | 1.08 |
| Crude Soy, AN 1.4 | 0.5" × 12" | Base Acitivated Clay 313 | 0.5 | 88% | 475 | 500 | 0.12% | 1.09 |
| Crude Soy, AN 1.5 | 0.5" × 12" | Base Acitivated Clay 313 | 0.5 | 35% | 475 | 500 | 0.80% | 0.92 |
| Crude Soy, AN 1.5 | 0.5" × 12" | Base Acitivated Clay 313 | 0.3 | 88% | 475 | 250 | 0.12% | 1.33 |
| Crude Soy, AN 1.4 | 0.5" × 12" | Base Acitivated Clay 326 | 0.5 | 20% | 500 | 500 | 0.79% | — |
| Crude Soy, AN 1.4 | 0.5" × 12" | Base Acitivated Clay 327 | 0.5 | 35% | 800 | 500 | 0.82% | — |
| Crude Soy, AN 1.4 | 0.5" × 12" | Acid Acitivated Clay | 0.5 | 35% | 500 | 725 | 0.75% | 6.00 |
| Crude Soy, AN 1.4 | 0.5" × 12" | Stainless Steel. "0.03" spheres | 0.5 | 35% | 475 | 050 | 1.04 | 0.90 | feedstock 16 and alcohol 18 moving in the same direction (co-flow). Additionally, minimal amounts of excess alcohol may be used to sweep byproduct water out the top of the reactor minimizing alcohol usage and the product's acid number (maximizing conversion percentage, such as from over about 50, about 75, about 100, to up to around 300, to less than about 1, 0.7, 0.5, 0.3 or even 0.1) while potentially maximizing alkyl ester yield.

There are several variations in which one or more of these countercurrent packed columns may be employed based on the feedstock and other process requirements. This process can be implemented as an esterification-only system, an alcoholysis-only system, a hydrolysis-only system, hydrolysis/esterification system or an esterification/alcoholysis system.

When implemented for esterification only, the process could likely be employed to process feedstocks having an acid number in excess of 0.5, 100, or even around 300. If the feedstock is sufficiently high in free fatty acids, the esterification process may be all that is required, but in many cases could be preceded by or followed by a transesterification step—conventional or otherwise. When the process is implemented as esterification-only, a single packed, countercurrent column could be employed wherein the packing is a heterogeneous catalyst meeting the description of that outlined herein.

When performing the esterification step, it is preferable, for at least some embodiments to convert to an Acid Number (AN) of less than 30, less than 8, less than 2, less than 0.5, or even less than 0.2. Some embodiments have been found to convert from over 30, or even over 100, to an Acid Number less than 0.5, or even less than 0.2 in a single stage process. Still other embodiments have achieved conversion to less than about 0.05 for an acid number.

When implemented for transesterification—only, the process could likely be employed to process feedstocks having an acid number of less than but not limited to 0.5. When the The process may also be implemented as two or more packed, columns operated in series, possibly with separation of free glycerin between each successive column. When the process is implemented as hydrolysis—only a single packed, countercurrent column could be employed wherein the packing is a heterogeneous catalyst meeting the description of that described herein.

The process proposed herein may be implemented as either a single column with one or more reaction zones OR two or more separate columns in order to perform both hydrolysis and esterification on a particular feedstock. In the two or more column configuration a hydrolysis only column could be followed by an esterification-only column allowing for separation of free glycerin between the columns. Some embodiments may utilize a single reactor 10.

A single column, possibly with multiple reaction zones, can also be employed in which a hydrolysis zone at the top of the column is followed by an esterification at the bottom of the column. The top zone would be packed with a catalyst best suited for hydrolysis while the lower zone would be packed with a catalyst best suited for esterification, although a single catalyst may also be employed for both functions, possibly performing one step better than the other. The hydrolysis zone, possibly near the top of the column would be maintained with some moderately high concentration of water. As feedstock flows through the top zone any glycerides are hydrolyzed and the resulting free fatty acids enter the esterification zone of the reactor wherein alcohol vapor flowing from the bottom of the reactor react with the fatty acids forming alkyl esters and excess alcohol is used to return the byproduct water to the top of the column.

The process proposed herein may be implemented as either a single column with one or more reaction zones or two or more separate columns in order to perform both transesterification and esterification on a particular feedstock. In a two or more column configuration an esterification-only column could be followed by an alcoholysis-only column.

A single column with multiple reaction zones can also be employed in which a transesterification zone at the top of the column is followed by an esterification zone at the bottom of the column or visa versa. The top zone could be packed with a catalyst best suited for transesterification while the lower zone could be packed with a catalyst best suited for esterification, although a single catalyst may also be employed for both functions. As feedstock flows through the top zone any free fatty acid glycerides are esterified and the resulting alkyl esters and remaining glycerin enters the esterification zone of the reactor wherein alcohol vapor flowing from the bottom of the reactor react with the fatty acids forming alkyl esters and excess alcohol is used to carry water produced in the esterification zone out the top of the reactor.

Each of the above configurations in this section presented an implementation wherein the catalyst served as the column packing. Another physical implementation that may be apply to all other implementations in the section is one in which the column is coarsely packed with an inert packing and the heterogeneous catalyst is mixed with the feedstock prior to entering the column. Alcohol vapor can be flowed from bottom to top still maintaining a counter current column. The catalyst exits the column with the product and can thereafter be filtered from the product.

Esterification/transesterification may also have the added benefit of deionization of the resultant alkyl esters, possibly to a high degree, if not completely, somewhat akin to running water through ion columns of both acidic and basic tendancies in an effort to provide deionized water.

The process proposed herein can employ the use of any lower alcohol. Most notably are methyl, ethyl, isopropyl, and butyl alcohols.

While most catalysts tested seem to provide some activity for both transesterification and esterification, optimized catalysts for each transesterification and esterification can provide the most effective and efficient overall process as desired by the user.

Esterification processes preferably employees the use of esterification catalysts that are: acid activated clays, such as diatomaceous earth, which may take the form of powders, granules, etc., which are acid activated, such as by soaking in a selected acid bath for a period of time and baking. Citric acid, sulfuric acid, phosphoric acid and/or other acids have been found effective such as if soaking for about two hours or other time period and then baking for hours such as about 8-12 hours or other appropriate temperature, porous clays may preferably have 50-80% or more of the pore sizes in excess of 50 Å, if not 75 Å or even larger, such as up to or maybe even exceeding 200 Å, and/or either granular, powder and/or other consistency.

An alcoholosis process preferably employees the use of alcoholysis catalysts that are: Base activated clays which may take the form of powders, granules, etc., which are base activated, such as by soaking in a selected bases bath for a period of time and baking. Sodium Hydroxide, potassium hydroxides, calcium hydroxides, magnesium hydroxides, and ammonia and/or other bases have been found effective such as if soaking for about two hours or other time period and then baking for hours such as about 8-12 hours at appropriate temperatures, porous clays may preferably have 50-80% or more of the pore sizes in excess of 50 Å, if not 75 Å or even larger, such as up to or maybe even exceeding 200 Å, and/or either granular, powder and/or other consistency may be employed.

Hydrolysis processes preferably employees the use of hydrolysis catalysts that are: acid activated clays which may take the form of powders, granules, etc., which are acid activated, such as by soaking in a selected acid bath for a period of time and baking. Citric acid, sulfuric acid, phosphoric acid and/or other acids have been found effective such as if soaking for about two hours or other time period and then baking for hours such as about 8-12 hours at 800-900 C or other appropriate temperature, porous clays may preferably have 50-80% or more of the pore sizes in excess of 50 Å, if not 75 Å or even larger, such as up to or maybe even exceeding 200 Å, either granular, powder and/or other consistency.

The process provides appreciable levels of completion or conversion without significant thermal degradation of reactants can be in the range of about 150 C to about 330 C. Other embodiments may use other temperature ranges inside, or outside, or overlapping this range. The optimal temperature range when the preferred catalyst was used as the catalyst is 220 C to 240 C, but other temperatures may be desirable under other conditions or situations.

The proposed process may perform better at elevated pressure up to and including high pressure applications (exceeding 500 psi or even 2000 psi), however, with elevated pressures come increased equipment costs. Many embodiments of the process are expected to operate in the range of 0-500 psig. The rates of reaction typically increase with increasing pressure across this pressure range as do equipment costs. The optimal pressure range may be 150-300 psig based on balancing equipment costs and rates of reaction, but other embodiments may operate in different ranges or pressure points.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A method comprising the steps of:
   providing a single reactor containing (a) a feedstock having at least one of free fatty acids and bound glycerides, (b) a monohydric aliphatic alcohol, and (c) at least one catalyst selected from the group of activated clay, activated diatomaceous earth, silica zeolite, NiO on Aluminum substrate alloys of steel containing nickel, stainless steel, nickel, palladium, palladium on Aluminum substrate, platinum, iron, zinc, alumina substrate and aluminum catalysts, at a pressure less than the supercritical pressure of the alcohol;
   wherein said single reactor performs the steps selected from the group of (a) transesterification, (b) esterification, and (c) simultaneously performing the steps of transesterification as well as esterification, wherein (i) the fatty acid glycerides are converted into alkyl esters with the transesterification process, if performed, and (ii) free fatty acids are converted into alkyl esters with the esterification process, if performed, to achieve a conversion in the reactor of Acid Number (AN) from at least about 30 to less than about 1; and
   wherein the process is performed as a continuous process in the single reactor.

2. The method of claim 1 wherein the reactor provides a flow of the feedstock from a first direction, and a flow of the alcohol from a second direction and wherein the first direction is with the second direction in a co-flow manner.

3. The method of claim 1 wherein the reactor provides a flow of the feedstock from a first direction, and a flow of the alcohol from a second direction and wherein the first direction against the second direction in a counter-flow manner.

4. The method of claim 1 wherein a product is continually discharged from the reactor containing alkyl esters and released glycerin, and further comprising the step of mechanically separating the released glycerin from the alkyl esters.

5. The method of claim 3 wherein a port receives a vapor from the reactor, said vapor having unreacted alcohol and water therein.

6. The method of claim 1 when the alcohol is selected from the group of methyl, ethyl, isopropyl and butyl alcohol.

7. The method of claim 5 wherein a range of at least 10% to about 75% by weight alcohol as compared to the feedstock is provided to the reactor preferably about 0.2-0.3% by weight alcohol per percent free fatty acid present in the feedstock and about 0.2-0.4% by weight alcohol per percent fatty acid glyceride present in the feedstock.

8. The method of claim 1 wherein the catalyst provided is an activated clay with the clay having a surface area of 180 to 300 m2/g; a total pore volume of 0.5 to 0.7 ml/g; wherein at least 60% of the total pore volume are provided by pores having a pore diameter of at least 140 Å, at least 40% of the total pore volume is provided by pores having a pore diameter of less than 250 Å and at least 15% of the total pore volume are provided by pores having a pore diameter of 140 to 250 Å and less than 20% of the total pore volume is formed by pores having a diameter of >800 Å; a SiO2 content of between more than 60 wt. % and less than 75 wt. %; an aluminum content, calculated as Al2O3, of between less than 12 wt. % and more than 2 wt. %; and said clay material having an amorphous structure according to XRD data.

9. The method of claim 1 wherein the activated clay is acid activated with an acid selected from the group of phosphoric acid, sulphuric acid and citric acid, and the acid activation step occurs by depositing an acid on the clay and the amount of acid deposited on the clay material is selected within a range of 2 to 5 wt.-%, calculated as water-free acid and based on the weight of the dry clay material.

10. The method of claim 1 wherein the activated clay is base activated with a sodium, potassium, calcium, or magnesium form base, and the base activation step occurs by depositing a base on the clay and the amount of base deposited on the clay material is selected within a range of 10 to 40 wt.-%, calculated as water-free base and based on the weight of the dry clay material.

11. The method of claim 1 wherein free fatty acids are converted into alkyl esters with the esterification process, if performed, to achieve a conversion in the reactor of Acid Number (AN) less than about 8.

12. The method of claim 1 wherein free fatty acids are converted into alkyl esters with the esterification process, if performed, to achieve a conversion in the reactor of Acid Number (AN) less than about 2.

13. The method of claim 1 wherein free fatty acids are converted into alkyl esters with the esterification process, if performed, to achieve a conversion in the reactor of Acid Number (AN) less than about 0.2.

14. The method of claim 1 wherein the single reactor performs the step selected from the group of (a) transesterification, and (c) simultaneously performing the steps of transesterification as well as esterification.

15. The method of claim 1 wherein the catalyst is provided in a granular form.

* * * * *